United States Patent [19]
Ansari

[11] Patent Number: 5,082,371
[45] Date of Patent: Jan. 21, 1992

[54] METHOD AND APPARATUS FOR MEASURING ENTRAINED AIR IN CONCRETE

[75] Inventor: Farhad Ansari, Passaic, N.J.

[73] Assignee: New Jersey Institute of Technology, Newark, N.Y.

[21] Appl. No.: 458,285

[22] Filed: Dec. 28, 1989

[51] Int. Cl.$^5$ .................................................. G01N 21/49
[52] U.S. Cl. .................................. 356/446; 356/133; 250/574
[58] Field of Search ............... 356/337, 342, 338, 339, 356/345, 437, 440, 441, 28, 133, 335, 446; 250/227.11, 574, 227.27; 128/634, 635; 73/53, 61 R, 861.04

[56] References Cited
U.S. PATENT DOCUMENTS

| | | |
|---|---|---|
| 4,622,974 | 10/1986 | Coleman et al. ............... 128/634 |
| 4,623,789 | 10/1986 | Ikeda et al. ................. 250/227.11 |
| 4,659,218 | 4/1987 | de Lasa et al. ................... 356/28 |

Primary Examiner—Vincent P. McGraw
Assistant Examiner—LaCharles P. Keesee
Attorney, Agent, or Firm—Klauber & Jackson

[57] ABSTRACT

A device for measuring entrained air in concrete, includes a needle tube for insertion into the concrete, the needle tube having a distal end; an optical fiber extending through the needle tube to the distal end, with the end of the optical fiber and the distal end of the needle tube being ground to have a sharp conical angle; a laser diode which produces laser light; a coupling device which supplied the laser light from the laser diode to the optical fiber and which separates the light reflected back through the optical fiber; and a photodetector which converts the received light from the coupling device to an electrical signal corresponding to the intensity of the reflected light.

16 Claims, 8 Drawing Sheets 5,082,371

METHOD AND APPARATUS FOR MEASURING ENTRAINED AIR IN CONCRETE

BACKGROUND OF THE INVENTION

This invention relates generally to a method and apparatus for determining the amount of entrained air in freshly mixed concrete.

Deterioration of concrete structures due to freezing and thawing is one of the most significant problems in northern climates. Thus, major problems in concrete pavement such as scaling and spalling, pop-outs, D-line and pattern cracking, and the like are attributed to deteriorating effects of temperature extremes on concrete. Deterioration of concrete exposed to freezing and thawing is caused by hydraulic pressure generated by the expansion of freezing water in the capillary cavities of concrete. The magnitude of the hydraulic pressure depends on the distance between capillary pores and an escape boundary, such as an air void. In concrete, disruptive stresses will be developed, unless every capillary cavity in the paste is not farther than three or four thousandths of an inch from the nearest air void.

Ordinary concrete will contain a minimum of 1 percent of air voids. Experiments have indicated an expansion of 0.41 to 0.75 percent in concrete volume for a range of water to cement ratios at −4° F. Therefore, the amount of empty space in nearly all concrete is large enough to accommodate the extra volume required by freezing of water in the capillaries. However, since the empty space is not sufficiently near to all capillaries, frost action would deteriorate the concrete. To overcome this problem, entrained air is provided.

Specifically, entrained air concrete contains a large number of very small air bubbles and is several times as resistant to frost action as non-air entrained concrete made of the same materials. Such entrained air concrete should be a dense, impermeable mixture that is well placed, protected, finished and cured if maximum durability is to be obtained. Preferably, the air voids are more effective when they are close together, and the cement paste in the concrete is normally protected against the effects of freezing and thawing if the spacing factor of the air void system is 0.08 inches or less, as determined with ASTM C 457.

The air content and size distribution of air voids produced in air entrained concrete are influenced by many factors, including but not limited to, the nature and concentration of the air entraining admixture, the nature and proportions of the constituents of the concrete mixture, the type and duration of mixing employed, the consistency, and the kind and degree of compaction applied in placing the concrete.

Therefore, it is very important to control the quality of air entrained concrete during mixing and placing. More particularly, it is very important to provide a rapid and reliable procedure for determining the air void characteristics, particularly the distribution of entrained air in freshly mixed concrete. No method, to date, is known for such a rapid, reliable and non-destructive method of in-place monitoring of entrained air in concrete.

Since the percentage of entrained air in concrete must be carefully controlled because the freezing and thawing durability is impaired if the concrete contains an insufficient amount of air and the strength is unnecessarily reduced if the percentage of air becomes excessive, some testing still must be performed for the same. Some common methods used to determine the air content in freshly mixed concrete are the volumetric method, gravimetric method and the pressure method.

In the volumetric method, a known volume of concrete is removed from the mix and mixed with water. The mixture is then agitated until the air separates from the slurry and a decrease in volume is then measured.

In the gravimetric method, the percentage of air is determined from the inverse relationship between the unit weight of concrete and the amount of entrained air.

In the pressure method, air which has been pumped to a predetermined pressure in a compartment of known volume is released into a sealed container full of concrete. The pressure-volume relationship or Boyle's law is then used to measure the amount of air.

However, none of these known tests can be used in situ. Rather, all of these methods must be performed in the laboratory. Further, such laboratory tests take anywhere from between one-half to one hour to perform. By that time, the concrete has already dried in place and is difficult to remove if the laboratory tests indicate that the air content is not satisfactory. Further, the in situ characteristics of the air entrained concrete may be quite different from the laboratory measured amount. Further, it is desirable to be able to measure the amount of entrained air at several locations in a pavement slab while it is being placed, in order to assure uniformity of the mix throughout the pavement. This cannot be performed with the laboratory tests.

OBJECTS AND SUMMARY OF THE INVENTION

Accordingly, it is an object of the present invention to provide a method and apparatus for measuring entrained air in concrete that overcomes the aforementioned problems with the prior art.

It is another object of the present invention to provide a method and apparatus for measuring entrained air in situ in freshly mixed concrete.

It is still another object of the present invention to provide a method and apparatus for measuring entrained air in concrete that is non-destructive, reliable and can be rapidly performed on site.

It is a further object of the present invention to provide a method and apparatus for measuring entrained air in concrete which can provide savings in millions of dollars in future expenditures in highway systems.

It is a still further object of the present invention to provide a method and apparatus for measuring entrained air in concrete that is relatively easy and economical to make and use.

In accordance with an aspect of the present invention, a device for measuring entrained air in freshly mixed concrete includes light transmission means for supplying light into the concrete and for receiving the light that is reflected back; and conversion means for converting the received light to an electrical signal corresponding to the intensity of the reflected light.

In accordance with another aspect of the present invention, a device for measuring entrained air in freshly mixed concrete includes needle means for insertion into the concrete, the needle means having a distal end; light transmission means, in the needle means and extending to the distal end, for supplying light thereto and for receiving light that is reflected back; and conversion means for converting the received light to an electrical signal corresponding to the intensity of the reflected light.

A method for measuring entrained air in freshly mixed concrete includes the steps of inserting light transmission means in the concrete; supplying light into the concrete through the light transmission means; receiving the light that is reflected back, in the light transmission means; and converting the received light to an electrical signal corresponding to the intensity of the reflected light.

The above and other objects, features and advantages of the present invention will become readily apparent from the following detailed description which is to be read in connection with the accompanying drawings.

DETAILED DESCRIPTION OF A PREFERRED EMBODIMENT

The present invention uses an optical fiber which is inserted into freshly mixed concrete to determine the amount of air bubbles therein.

Specifically, the present invention is based on the fundamental theory of Snell's law of refraction and reflection. According to Snell's law, if the light wave travels from a material with a higher refractive index into a material with a lower refractive index, most of the light is reflected back, whereas if the refractive indices are the same or almost the same, most of the light will enter the new medium and will not be reflected back. As a result, where the refractive indices are similar, there will be a large intensity loss of reflected light which can be accurately measured.

Figure 1:
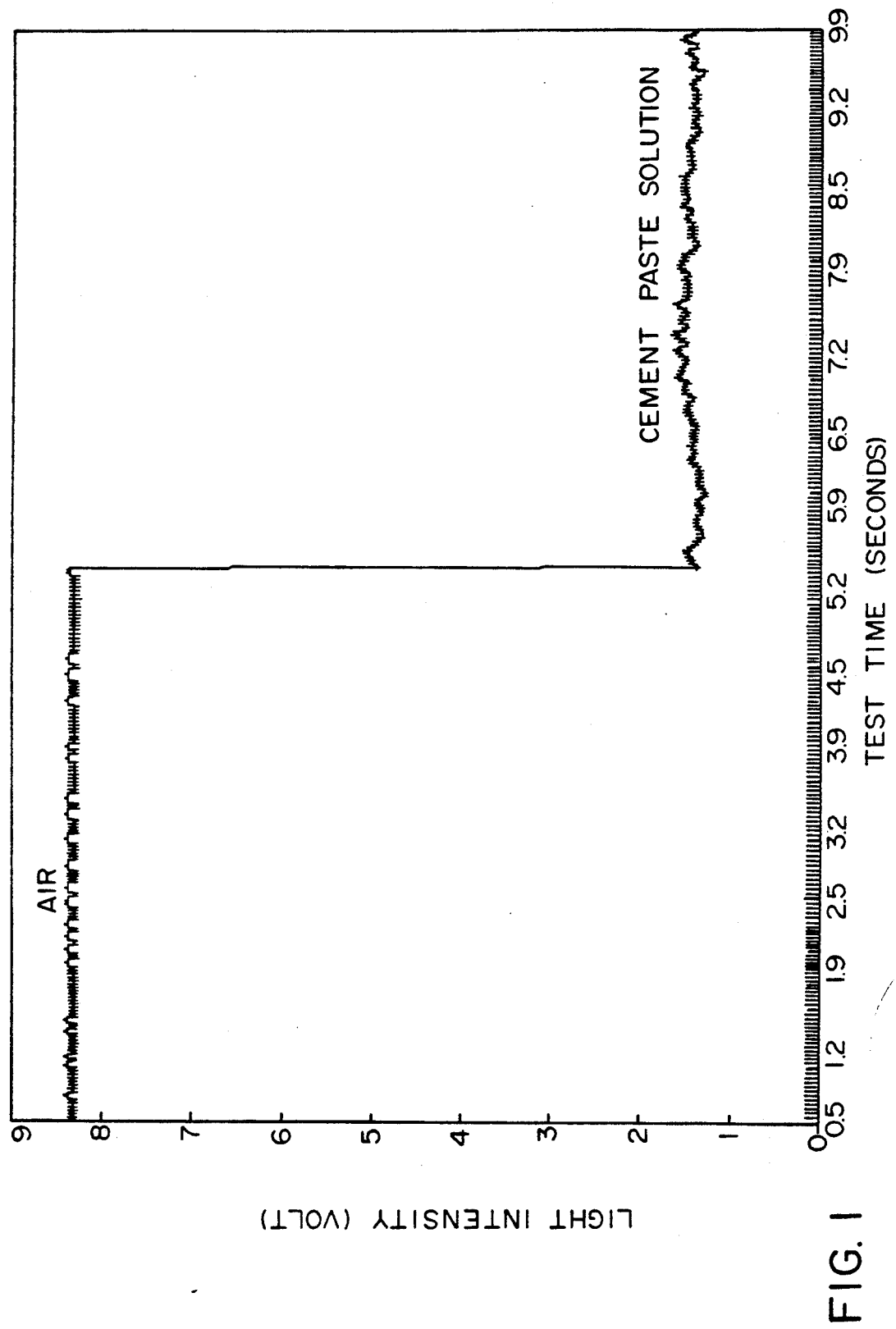
FIG. 1 is a graphical diagram showing the difference in reflected light intensity when light is transmitted from an optical fiber into air and a cement paste solution.
Figure 2:
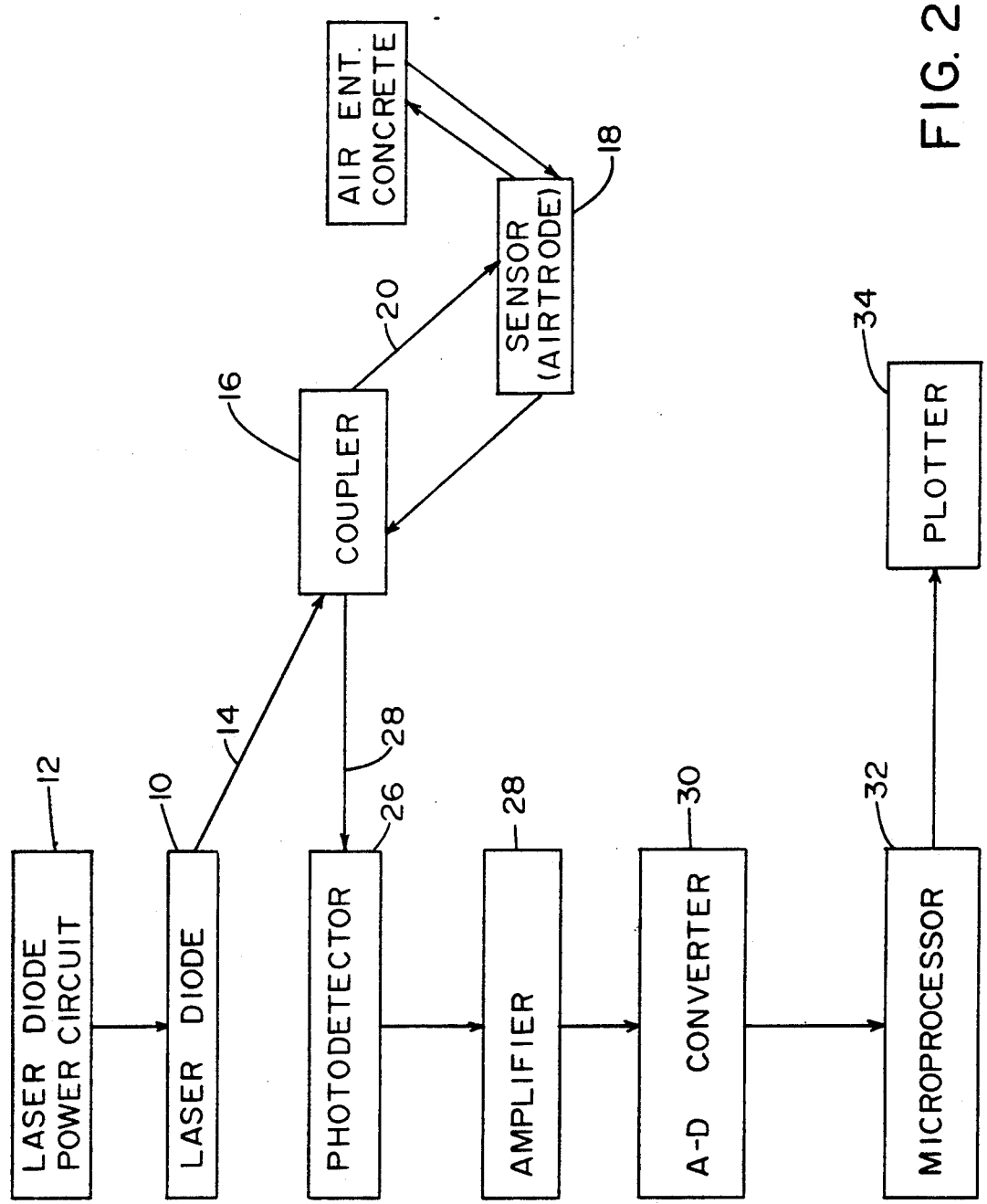
FIG. 2 is a block diagram of apparatus according to one embodiment of the present invention.
Figure 3:
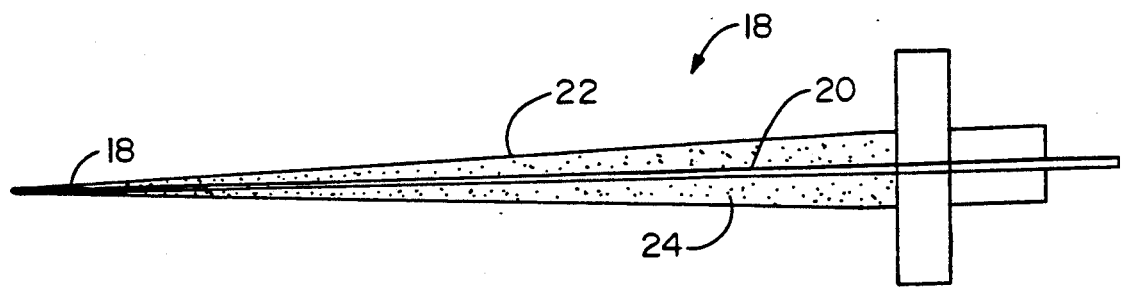
FIG. 3 is a schematic drawing of the sensor used in the apparatus of FIG. 2.
Figure 4:
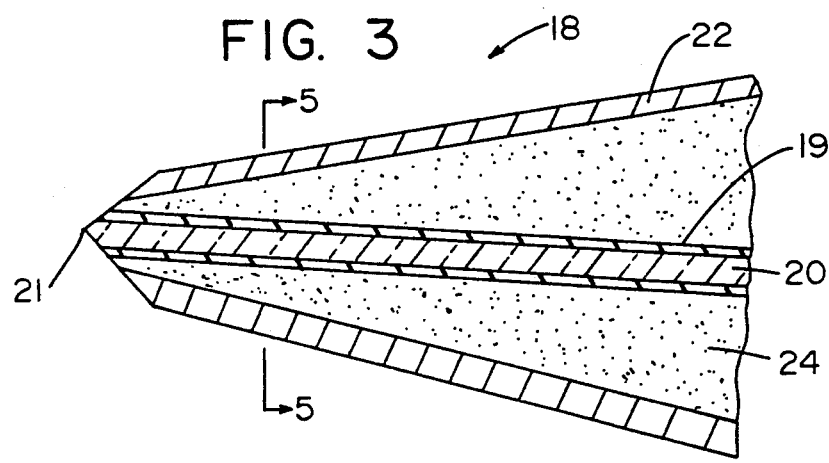
FIG. 4 is an enlarged longitudinal cross-sectional view of the distal end of the sensor of FIG. 3.
Figure 5:
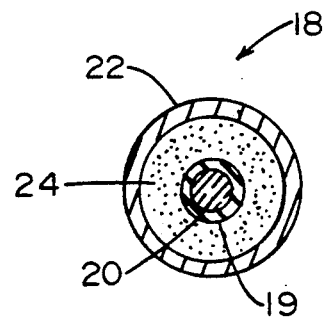
FIG. 5 is a cross-sectional view of the sensor of FIG. 4, taken along line 5—5 thereof.

The refractive index of an optical fiber will generally range between 1.3 to 1.7, depending on the material used in fabrication of the optical fiber. Assuming, for example, that a typical optical fiber has an index of refraction of 1.44, if the light exiting an end of such optical fiber meets an air bubble having an index of refraction of 1.0003 inside the fresh concrete, due to the higher refractive index of the optical fiber, most of the light will reflect back. This is virtually the same as if the optical fiber is used in the open air. On the other hand, since a cement paste solution has a refractive index of 1.3, which is close to that of the optical fiber material, much of the light is transmitted out of the fiber into the concrete. The difference in detected light intensity from the reflected light in such situation is shown in FIG. 1. In other words, high intensity reflections indicate air bubbles, and low intensity measurements suggest the absence of air bubbles in freshly mixed concrete.

It will also be appreciated that the angle by which the light ray strikes the interface between the two mediums, that is, the angle of incidence, also plays an important role in controlling the amount of refraction and reflection. This angle is measured with respect to a line perpendicular to the interface. Thus, larger angles of incidence bring about more reflected rays, whereas sharper angles give rise to further refraction.

In accordance with a preferred embodiment of the present invention, a battery powered laser diode 10 which preferably emits visible light having a wavelength of 670 nm is employed for transmitting the optical signals. It will be appreciated, however, that the light source need not be a laser light source. Laser diode 10 is powered by a laser diode power circuit 12 which can be constituted by a battery. An optical fiber 14 supplies the light from laser diode 10 to a coupler 16 which directs the signal to the exit end of an optical fiber 20 (having cladding 19 therearound) in a sensor 18, which is inserted within the freshly mixed concrete.

Sensor 18 is specially designed to provide continued measurements with optical fiber 20, without the problem of the freshly mixed cement paste binding to the surface end of the optical fiber, which would prevent the device from sensing air bubbles in the freshly mixed concrete. Therefore, to reduce the attractive forces at the cement paste-fiber surface interface, the already small cross-sectional surface of the fiber end, for example, of a 50 micron diameter, is further reduced. Specifically, one way of reduction is to heat the optical fiber by a direct flame while it is pulled on both sides in order to create a needle-shaped small surface area at the fiber end. Thus, while creating a very small surface area, the speed by which sensor end 18 responds to change in indices is further increased, primarily due to the taper created at the fiber end. Further, there is no problem of bonding between the cement paste and the fiber end with such arrangement, and experiments have shown great accuracy in sensing the number of air bubbles.

Because of the small diameter thereof, however, in order to prevent breakage of the bare fiber inside the freshly mixed concrete, it is preferred that sensor 18 includes a fine gauge stainless steel syringe needle tube 22, with optical fiber 20 being inserted into needle tube 22. As an example, optical fiber 20 can have a diameter of 100 microns, while needle tube 22 has a diameter of 200 microns. Optical fiber 20 is held fixed inside needle tube 22 by filling needle tube 22 with an epoxy 24 that surrounds optical fiber 20. Because optical fiber 20 includes cladding 19, there is no loss of the light signal, and epoxy 24 therefore need not have the same refractive index as optical fiber 20. A suitable epoxy that can be used is Archer Brand Quick Setting Epoxy, Catalog No. 64-2313A, custom manufactured for the Radio Shack Division of Tandy Corporation, Fort Worth, Tex. 76102. Then, the common ends of optical fiber 20 and needle tube 22 are ground to a sharp angle in a conical configuration, so that optical fiber 20 is exposed only at the point or tip 21 thereof. Thus, there is no need to use a flame to reduce the optical fiber. The sharper tip 21, the better the construction. Accordingly, the angle of incident light is decreased and thereby provides faster reflected signals due to the air bubbles. Further, the sharp fiber tip is strengthened by the surrounding needle tube 22.

The reflected light is transmitted back through optical fiber 20 and coupler 16 to a photodetector 26 through another optical fiber 28. In other words, coupler 16 separates the reflected and transmitted signals and directs the reflected signal to photodetector 26. Photodetector 26 converts the reflected light intensity signal to an electric current corresponding to such intensity, and such signal is then amplified by an amplifier 28 and converted to a digital signal by an analog-to-digital (A/D) converter 30.

Real-time data is then transferred to a computer, such as a PC (personal computer) for data processing in order to determine the percentage of air in the freshly mixed concrete. An IBM compatible computer can be used for computer 32. In order to provide on-site measurements, however, a portable hand-held computer can be used, such as a Toshiba lap top Model No. 1200 HB computer. Computer 32 can then supply a signal to a plotter 34 or the like in order to print the desired results or to display the same on a screen.

As a result, on-site determinations of the amount of air in freshly mixed concrete can be determined. If it is determined that the level is too low, an air entraining agent can be added to the concrete to increase the amount of air therein prior to pouring the same. A suitable air entraining agent that can be used is a resin sold under the designation MB-VR, manufactured by Master Builders, Inc., 55 Penn Drive, William Penn Business Center, Allentown, Pa. 18106.

Figure 6:
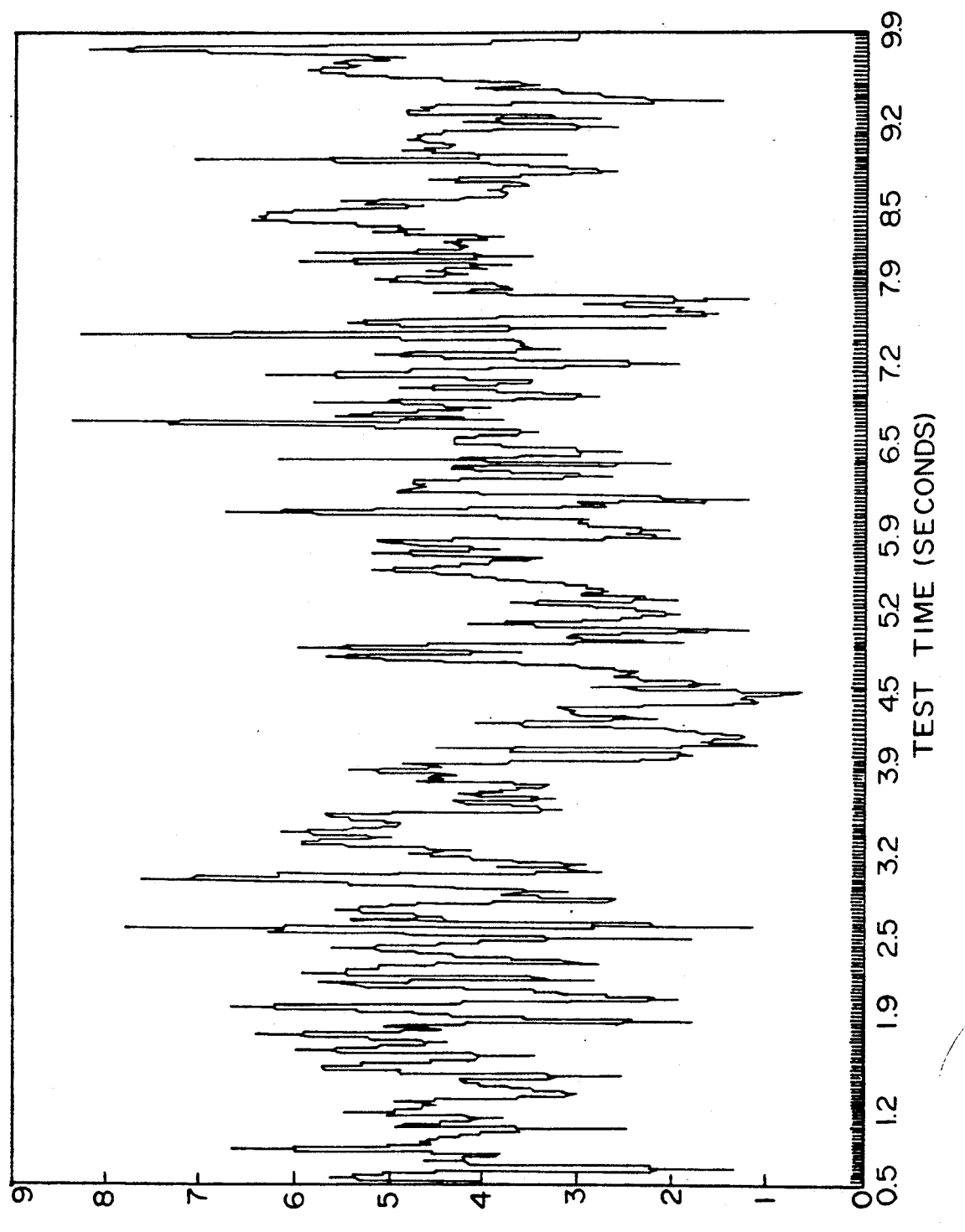
FIG. 6 is a graphical diagram showing reflected light with the sensor inserted in freshly mixed concrete, without an air entraining agent therein.
Figure 7:
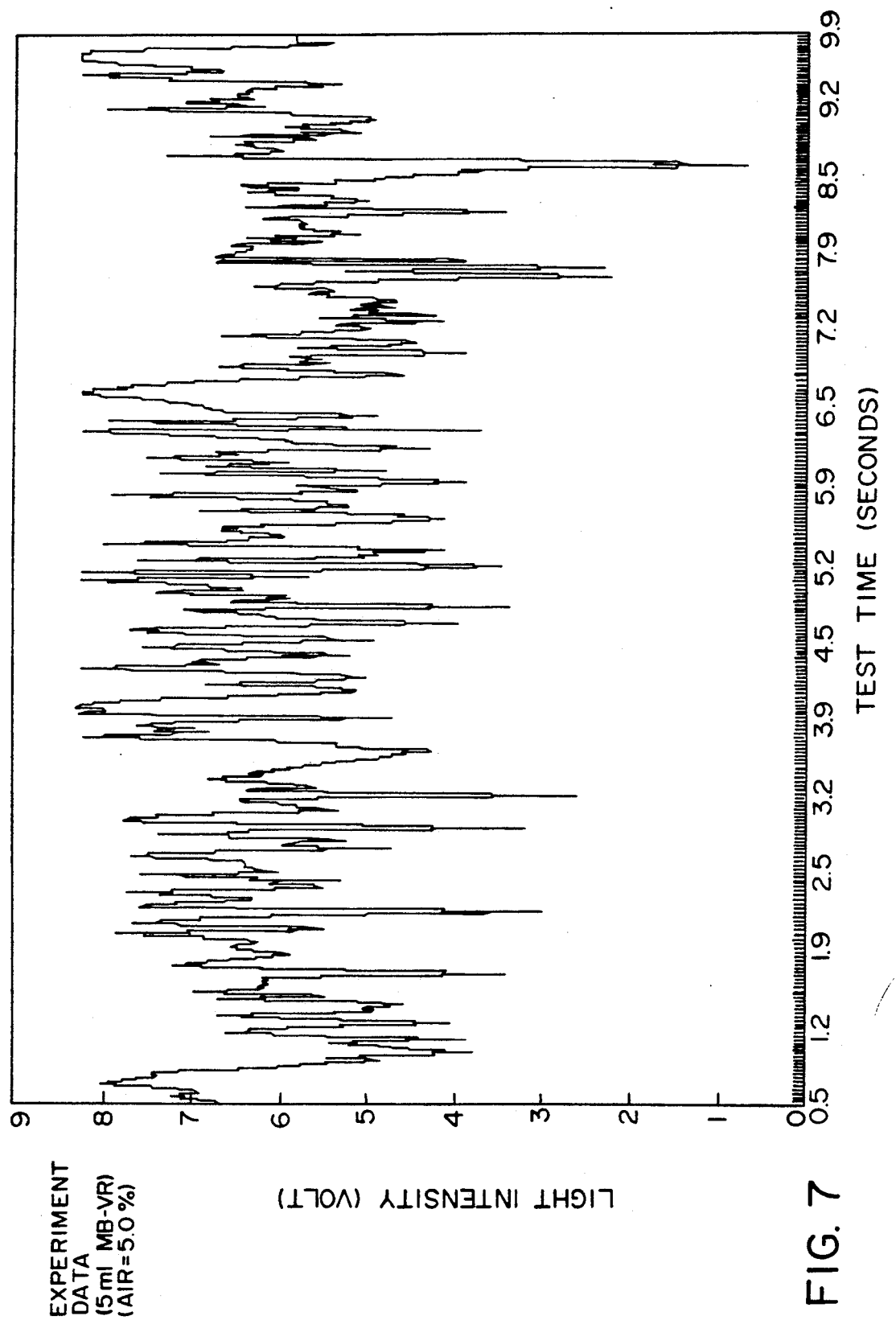
FIG. 7 is a graphical diagram similar to FIG. 4 with an air entraining agent in the concrete.

Specific experimental data showing a computer output from sensor end 18 without air entraining agent is shown in FIG. 6, while a similar higher light intensity reading is shown with the air entraining agent in FIG. 7.

Figure 8:
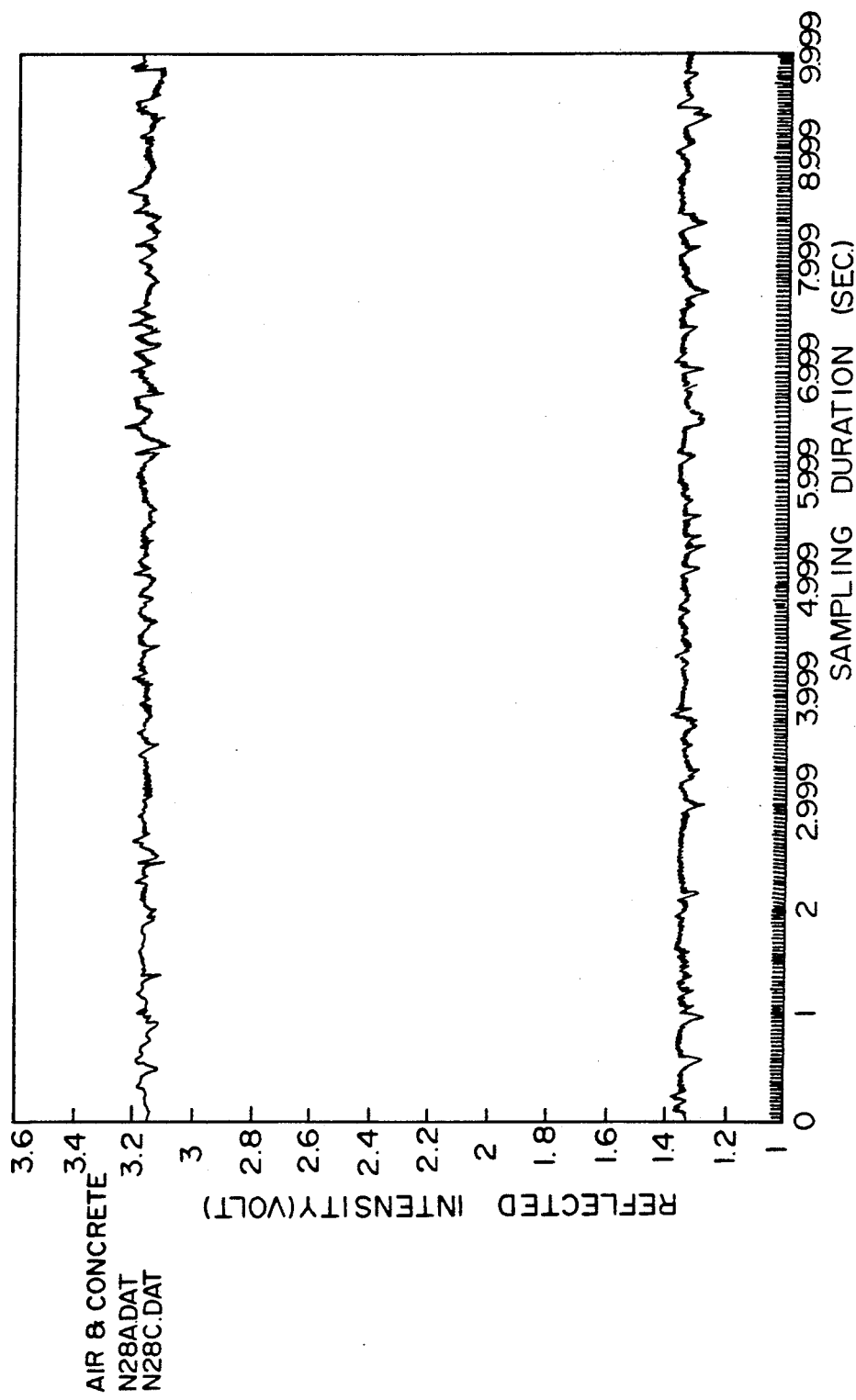
FIG. 8 is a graphical diagram used for showing the calculation of the percent air in the freshly mixed concrete according to the present invention.

One way of determining the amount of air in freshly mixed concrete from the various readings will now be explained with reference to FIGS. 8-10. Specifically, assuming that the optical fiber is placed in the open air for a period of ten seconds, or any other suitable time period, a horizontal line reading, similar to the air reading of approximately 8.3 volts of FIG. 1 will be obtained for the entire ten seconds. For example, this is shown by the upper horizontal line on the graph of FIG. 8, which provides a voltage reading of 3.1760 volts. It will be appreciated that the voltage readings will vary with the initial settings of amplification. Then, the optical fiber is placed in the cement paste solution so that the end of the optical fiber is not in an air bubble. In such case, a reading is taken for ten seconds such that a constant voltage is obtained, for example, as shown by the 1.3737 voltage reading of FIG. 8. The two ten second readings are then superimposed upon each other, as shown in FIG. 8 so as to obtain an area for the ten seconds between the air light intensity reading and cement paste light intensity reading, that is, the area will be $(3.1760-1.3737) \times 10.0 = 18.023$. Then, the optical fiber is again positioned in the cement paste solution and moved therein, for example, in a straight line, for the same time period. During such movement, the optical fiber will provide readings of the various air bubbles therein, along with readings regarding the cement paste solution. Such readings are shown, for example, in FIGS. 9 and 10 (which are similar to the curves of FIGS. 6 and 7).

The area under the curve of the respective figure is determined by computer analysis or any other suitable method, and the ratio of the area under such curve to the total area of the rectangular block on the superimposed graph will be equal to the percent air in the cement paste solution.

In order to determine the area under the curve, it is first noted that during movement of the sensor in the cement paste solution, high frequency noise is generated, which must be removed. The high frequency noise is represented by the area under a line (not shown) effectively connecting the lower points of the curve. The high frequency noise is removed during data acquisition by a low pass filter at the amplification stage. To obtain the area under the curve representing the filtered data points, the trapezoidal or any other numerical integration scheme can be employed, in which the area between each two adjacent sampling points is determined by multiplying the time between the sampling points times the difference in voltages between the two adjacent sampling points, and dividing the same by two. The sum of all such areas provides the desired area, with the area corresponding to high frequency noise removed. In effect, this method of determining the desired area provides a low pass filtered area which removes the high frequency noise component. However, other methods can be used.

Thus, for example, if there are 300 sampling points in the ten second interval, the distance between each sampling point is 0.033. If the first sampling point has a voltage of 2.76 volts and the second sampling point has a voltage of 2.71 volts, the area between the first two sampling points is $((2.76-2.71) \times 0.033)/2 = 0.000825$. All of the areas are then computed for all adjacent sampling points, and the areas are summed. In the case of FIG. 9, the total area equals 0.6703. Then, this area is divided by the rectangular area of FIG. 8 to obtain a value of 3.724% air in the cement.

Figure 9:
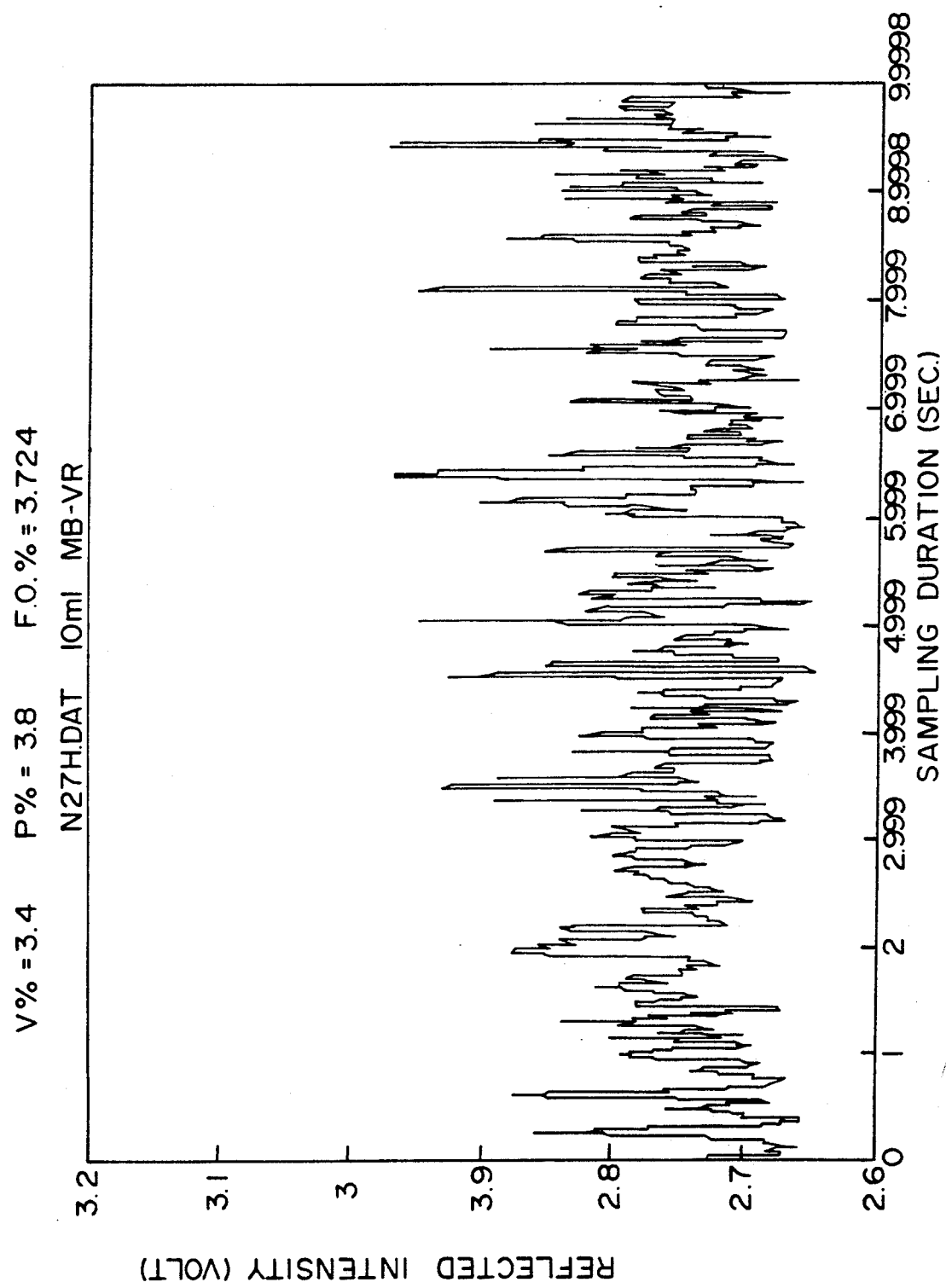
FIG. 9 is a graphical diagram used for showing the calculation of the percent air in the freshly mixed concrete according to the present invention.
Figure 10:
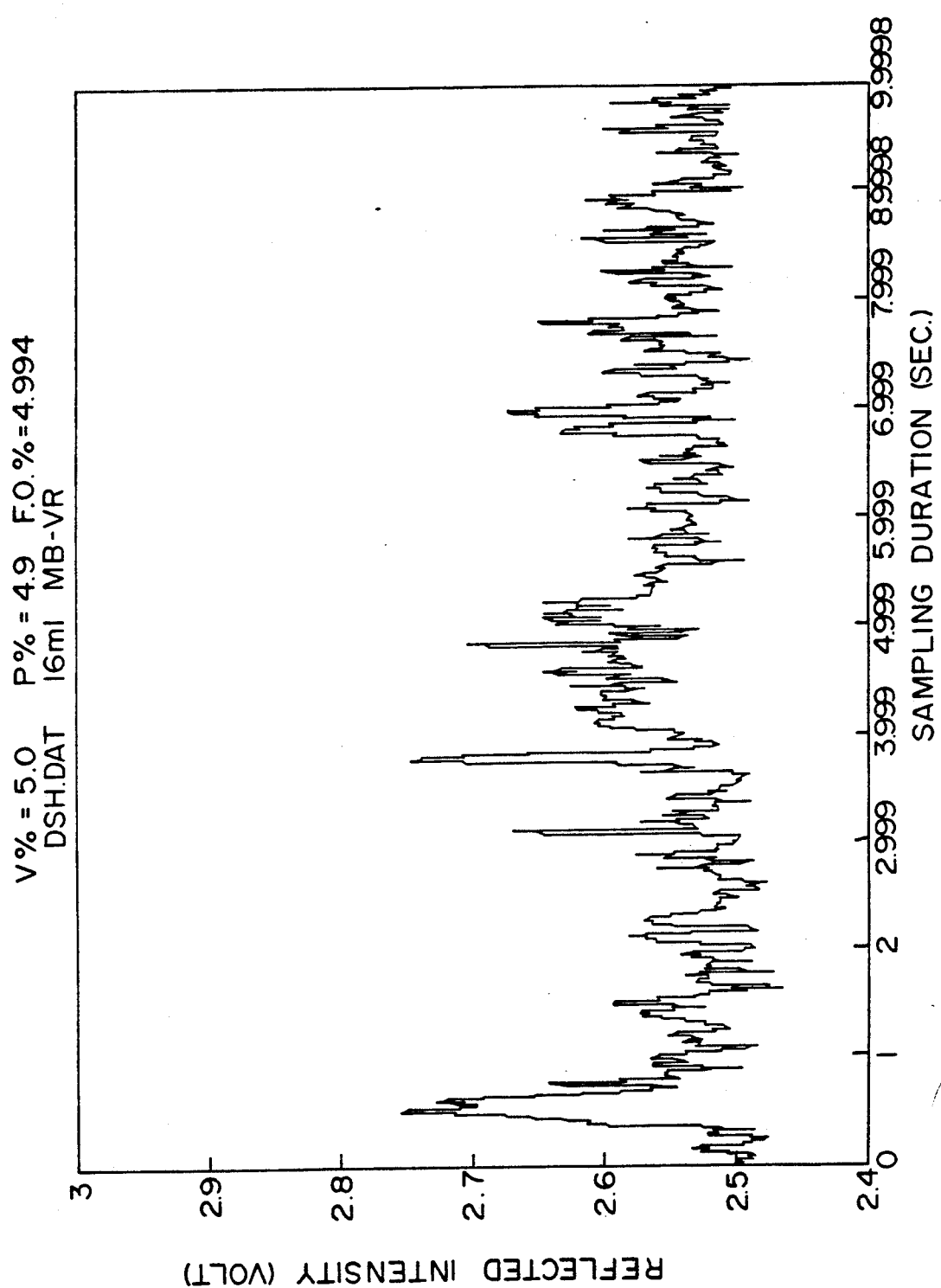
FIG. 10 is a graphical diagram used for showing the calculation of the percent air in the freshly mixed concrete according to the present invention.

It has been found that this percentage is substantially the same as determined by conventional laboratory methods, as shown by the measurements of 3.4% with the volumetric method and 3.8% with the pressure method, in FIG. 9.

Having described a specific preferred embodiment of the invention with reference to the accompanying drawings, it will be appreciated that the present invention is not limited to that precise embodiment, and that various changes and modifications can be effected therein by one of ordinary skill in the art without departing from the scope or spirit of the invention as defined by the appended claims.

What is claimed is:

1. A device for measuring entrained air in freshly mixed concrete, comprising:

light transmission means for supplying light into said concrete and for receiving said light that is reflected back, said light transmission means including a single optical fiber having a free distal end which is visibly exposed, said distal end having a tip with a sharp angle thereat; and conversion means for converting said received light to an electrical signal corresponding to the intensity of said reflected light.

2. A device according to claim 1, wherein said distal end has a substantially conical configuration.

3. A device according to claim 1, wherein said conversion means includes a photodetector.

4. A device according to claim 1, further including coupling means for separating said supplied light and said reflected light from said single optical fiber of said light transmission means.

5. A device according to claim 1, further including light supply means for supplying said light to said transmission means.

6. A device according to claim 5, wherein said light supply means includes a laser generator.

7. A device according to claim 5, wherein said laser generator includes a laser diode.

8. A device for measuring entrained air in freshly mixed concrete, comprising:
   needle means for insertion into the concrete, said needle means having a distal end;
   light transmission means, in said needle means and extending to said distal end, for supplying light thereto and for receiving said light that is reflected back, said light transmission means including a single optical fiber positioned in said needle means, said optical fiber having a visibly exposed end extending to said distal end, said visibly exposed end having a tip with a sharp angle thereat; and
   conversion means for converting said received light to an electrical signal corresponding to the intensity of said reflected light.

9. A device according to claim 8, wherein said distal end of said needle means and said end of said optical fiber each have a substantially conical configuration.

10. A device according to claim 8, wherein said conversion means includes a photodetector.

11. A device according to claim 8, further including coupling means for separating said supplied light and said reflected light from said single optical fiber of said light transmission means.

12. A device according to claim 8, further including light supply means for supplying said light to said transmission means.

13. A device according to claim 12, wherein said light supply means includes a laser generator.

14. A device according to claim 13, wherein said laser generator includes a laser diode.

15. A device according to claim 8, further including adhesive means for fixedly securing said light transmission means in said needle means.

16. A method for measuring entrained air in freshly mixed concrete, including the steps of:
   inserting a single optical fiber in the concrete such that a free distal end of said optical fiber is visibly exposed to said concrete and with said distal end having a tip with a sharp angle thereat;
   moving said optical fiber through said concrete;
   supplying light into said concrete through the optical fiber;
   receiving the light that is reflected back, in the optical fiber; and
   converting the received light to an electrical signal corresponding to the intensity of the reflected light.

* * * * *